United States Patent [19]

Aase

[11] Patent Number: 5,364,357
[45] Date of Patent: Nov. 15, 1994

[54] SMALL DIAMETER DILATATION CATHETER HAVING WIRE REINFORCED COAXIAL TUBULAR BODY

[75] Inventor: Brenda L. Aase, Eagan, Minn.

[73] Assignee: Schneider (USA) Inc., Plymouth, Minn.

[21] Appl. No.: 192,791

[22] Filed: Feb. 7, 1994

Related U.S. Application Data

[63] Continuation of Ser. No. 769,576, Oct. 2, 1991, abandoned, which is a continuation of Ser. No. 639,723, Jan. 9, 1991, abandoned, which is a continuation of Ser. No. 411,815, Sep. 25, 1989, abandoned.

[51] Int. Cl.⁵ .................. A61M 25/00; A61M 29/00; A61M 29/02
[52] U.S. Cl. ........................... 604/96; 604/282; 606/194
[58] Field of Search .................. 604/96–103, 604/280–283; 606/191–196; 128/656–658; 600/18

[56] References Cited

U.S. PATENT DOCUMENTS

| | | | |
|---|---|---|---|
| 2,268,321 | 12/1941 | Flynn | 604/282 X |
| 3,034,510 | 5/1962 | Kittel | 604/101 |
| 3,426,744 | 2/1969 | Ball | 604/96 X |
| 3,598,126 | 8/1971 | Hoeltzenbein | 604/282 |
| 3,908,664 | 9/1975 | Loseff | 604/96 |
| 4,299,227 | 11/1981 | Lincoff | 606/192 |
| 4,362,150 | 12/1982 | Lombardi, Jr. et al. | 604/99 X |
| 4,483,340 | 11/1984 | Fogarty et al. | 606/194 |
| 4,553,959 | 11/1985 | Hickey et al. | 604/96 |
| 4,706,670 | 11/1987 | Andersen et al. | 604/282 X |
| 4,733,652 | 3/1988 | Kantrowitz et al. | 604/96 X |
| 4,775,371 | 10/1988 | Mueller, Jr. | 604/280 |
| 4,776,844 | 10/1988 | Ueda . | |
| 4,784,636 | 11/1988 | Rydell | 604/22 |
| 4,784,651 | 11/1988 | Hickey | 604/282 |
| 4,817,613 | 4/1989 | Jaraczewski et al. | 128/658 |
| 4,823,805 | 4/1989 | Wojcik | 128/736 |
| 4,846,153 | 7/1989 | Berci | 128/6 |
| 4,898,591 | 2/1990 | Jang et al. | 604/282 |
| 4,906,241 | 3/1990 | Noddin et al. | 604/194 |
| 4,917,666 | 4/1990 | Solar et al. | 604/95 |
| 4,921,483 | 5/1990 | Wijay et al. | 604/96 |
| 4,976,720 | 12/1990 | Machold et al. . | |
| 5,041,089 | 8/1991 | Mueller et al. | 604/96 |

FOREIGN PATENT DOCUMENTS 8806465  9/1988  WIPO ................... 604/96

OTHER PUBLICATIONS

*Bard Hospital division Catalog of Products.* Bard Hospital division, Murray Hill, N.J. 07974. 1973, p. b10.
"The Surgical Armamentorium": American V. Mueller instruments and professional equipment catalog. 1980, American Hospital Supply Corp., p. 435.

*Primary Examiner*—C. Fred Rosenbaum
*Assistant Examiner*—Adam J. Cermak
*Attorney, Agent, or Firm*—Haugen and Nikolai

[57] ABSTRACT

A small diameter dilatation catheter for coronary angioplasty is achieved by providing first and second elongated flexible, thin-wall tubes, each having one or more reinforcing wires encapsulated in the walls thereof and dimensioned such that the second tube may be coaxially disposed within the lumen of the first tube. The preferred material from which the two tubes are fabricated is polyimide. The longitudinally extending reinforcing wires provide the requisite "pushability" characteristics required by PTCA dilatation catheters. The balloon or inflation member has its proximal end bonded to the outer surface of the outer tube and its distal end bonded to the outer surface of the inner tube. Inflation fluid then may be perfused between the I.D. of the outer tube and the O.D. of the inner tube.

15 Claims, 1 Drawing Sheet

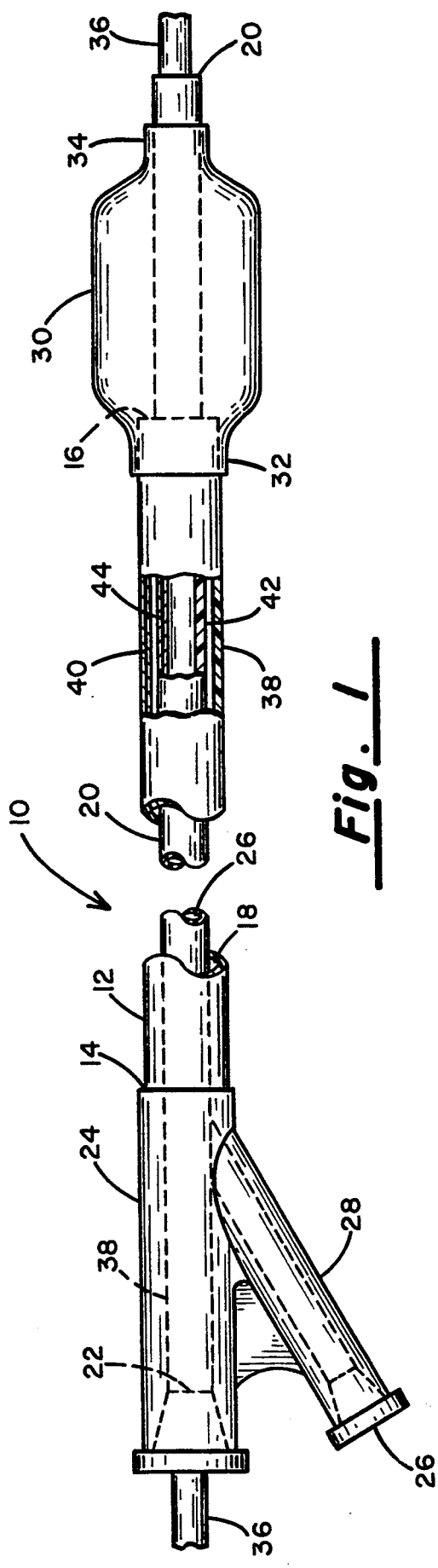
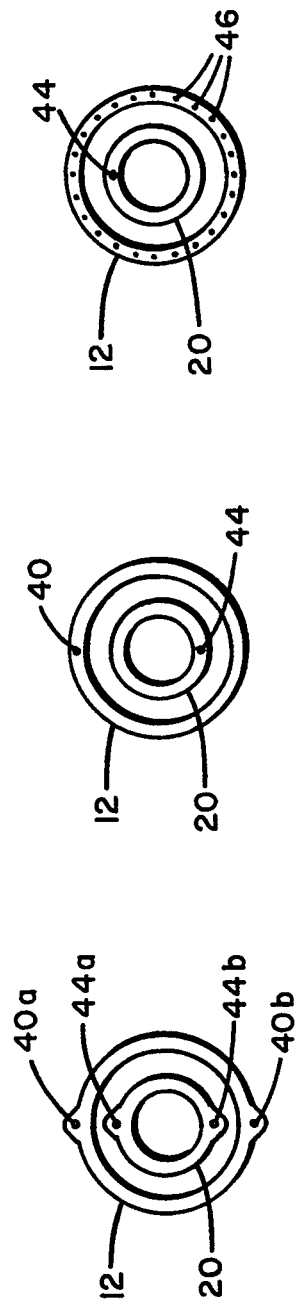

SMALL DIAMETER DILATATION CATHETER HAVING WIRE REINFORCED COAXIAL TUBULAR BODY

This is a continuation of copending U.S. patent application Ser. No. 07/769,576 filed Oct. 2, 1991 (now abandoned), which is a continuation of U.S. patent application Ser. No. 07/639,723 filed Jan. 9, 1991 (not abandoned), which is a file wrapper continuation of prior complete U.S. patent application Ser. No. 07/411,815, filed Sep. 25, 1989 (now abandoned).

BACKGROUND OF THE INVENTION

I. Field of the Invention

This invention relates generally to dilatation catheters for use in carrying out percutaneous transluminal coronary angioplasty (PTCA) procedures and more specifically to such a catheter which is designed to have a catheter body of very low diameter while still possessing the requisite firmness allowing it to be advanced through the vascular system without kinking or accordion pleating.

II. Discussion of the Prior Art

The PTCA procedure for restoring patency to occluded or partially occluded coronary arteries is generally attributed to A. Gruntzig. As is now well known, the procedure involves inserting an elongated tubular catheter having a balloon or expander member on its distal end into the vascular system and then advancing the catheter until the balloon spans or bridges the stenosis to be treated. Then, an inflation fluid is injected through the distal end of the catheter and made to perfuse along the length thereof to inflate the expander member to a predetermined size and pressure.

Since the procedure was first introduced, considerable work has gone on in developing improved catheters for carrying out this procedure. Much of the effort on the part of various catheter manufacturing companies has been in attempting to reduce the overall diameter of the catheter so that it may more readily be passed through small diameter coronary blood vessels. When it is also considered that a PTCA catheter must be used in combination with a guide wire which extends completely through the length of the catheter, the catheter shaft requires two lumens. The two lumens may be created by extruding or otherwise forming a double lumen tube or, alternatively, by providing two concentrically disposed tubes where the lumen of the centermost tube accommodates the guide wire and the passage between the O.D. of the inner tube and the I.D. of the outer tube allows for the perfusion of inflation fluid to the balloon.

In striving for low catheter shaft diameters, the wall thickness of the tubes becomes a critical factor. If made overly thin, the resulting catheter lacks sufficient longitudinal rigidity and tends to fold upon itself when an effort is made to push the PTCA catheter through its guide catheter. Thus, a practical limit exists on the minimum wall thickness while still permitting the necessary "pushability" characteristic necessary for advancing the catheter through the vascular system.

It is accordingly a principal object of the present invention to provide an improved PTCA catheter whose tubular body dimension is substantially smaller than any known prior art catheter for the same purpose presently on the market.

Another object of the invention is to provide a small diameter, thin-wall PTCA balloon catheter which exhibits sufficient longitudinal rigidity to allow it to be passed through the vascular system without kinking or pleating.

A further object of the invention is to provide a balloon catheter for use in PTCA procedures of the type including two coaxially disposed tubes of thin wall dimension, yet appropriately reinforced against accordion pleating when the catheter assembly is pushed through a guide catheter and into a blood vessel to be treated.

SUMMARY OF THE INVENTION

The foregoing features and advantages of the invention are achieved by providing first and second elongated flexible tubular members each of minimal wall thickness, the tubular members preferably being formed from a suitable polymer such as polyamide, polyester or polyimide with a polyimide plastic being preferred, and incorporating a reinforcing structure within the walls of one or both tubes. The tubes are coaxially disposed relative to one another with the smaller diameter tube having its distal end projecting beyond the distal end of the larger diameter tube. The inflatable expander member is circumferentially bonded at its proximal end about the distal end portion of the larger diameter tube and its distal end is circumferentially bonded to the distal end portion of the smaller diameter, concentrically disposed tube.

A molded plastic hub is affixed to the proximal ends of the two tubes and includes an inflation port in fluid communication with the annular space existing between the O.D. of the small diameter tube and the I.D. of the larger diameter tube. Inflation fluid injected through the inflation port then perfuses through this space to fill and inflate the expander member to a desired pressure. The lumen of the inner tube can accommodate a guide wire.

In accordance with a first embodiment of the invention, the reinforcing structure may comprise a single strand of wire extending substantially the entire length of the catheter and embedded within the wall of the larger diameter tube, the smaller diameter tube, or both. In another arrangement, plural strands of wire are incorporated in the wall of the tubes, either running parallel to one another or in a braided configuration.

DESCRIPTION OF THE DRAWINGS

The constructional features of the catheter of the present invention can be better perceived from the following detailed description of the preferred embodiments thereof, especially when considered in conjunction with the accompanying drawings in which:

FIG. 1 is a partially sectioned side elevation of a PTCA catheter constructed in accordance with the present invention;

FIG. 2 is a cross-sectional view of a catheter like that of FIG. 1 showing an alternative reinforcing structure;

FIG. 3 is another cross-sectional view illustrating yet another way of providing longitudinal reinforcement; and FIG. 4 is yet another cross-sectional view of a catheter like that of FIG. 1 except incorporating a still different reinforcing structure.

DESCRIPTION OF THE PREFERRED EMBODIMENT

Referring first to FIG. 1, the PTCA catheter constructed in accordance with the present invention is indicated generally by numeral 10. The catheter includes an outer tubular body member 12 having a proximal end 14 and a distal end 16 with a lumen 18 extending from the proximal end to the distal end.

Coaxially disposed within the lumen 18 of the outer tubular member 12 is an inner tubular member 20 having a proximal end 22 and a distal end 24 with a lumen 26 extending the full length thereof.

Affixed to the proximal end 14 of the outer tubular member 12 and the proximal end 22 of the inner tubular member 20 is a molded plastic hub 24 which is commonly referred to as a Y-connector. The connector includes a Luer fitting 26 at the end of a longitudinal bore passing through the arm 28 and in fluid communication with the annular space existing between the O.D. of the inner tube 20 and the I.D. of the outer tube 12.

Affixed to the distal end portion of the catheter 10 is an inflatable expander member 30. The expander member is also tubular in form and includes a proximal end 32 which is appropriately circumferentially bonded to the exterior wall surface of the outer tubular member 12. The distal end 34 of the expander member 30 is likewise appropriately bonded to the exterior wall surface of the inner tubular member 20 which extends outwardly beyond the distal end 16 of the outer tubular member. It can be seen, then, that when an inflation fluid is injected under pressure through the port 26, it will perfuse through the annular space between the two tubular members and will exit the distal end of the outer tubular member 12 into the interior of the inflatable expander member 30.

As is well known in the art, the expander member 30 may comprise a tubular film of polyethylene terephthalate (PET) which is biaxially oriented in a drawing and blow molding process so as to exhibit a very high burst strength well in excess of 100 PSI and which does not appreciably expand radially beyond a predetermined maximum diameter even with substantially increased pressures.

With continued reference to FIG. 1, there is also shown a guide wire 36 which passes through a bore 38 formed in the hub 24 and through the lumen 26 of the inner tube 20 so as to exit the distal end 24 thereof. Guide wires are commonly used in PTCA procedures for facilitating the steering of the catheter 10 through the vascular system to a location where the expander member 30 is disposed adjacent a stenotic lesion to be treated.

Referring to the sectioned portion of the catheter assembly 10 of FIG. 1, it will be noted that there is disposed within the wall thickness 38 of the outer tubular member 12 a reinforcing member 40 which, in FIG. 1, comprises a fine strand of wire, preferably stainless steel. The wall 42 of the inner tube 20 also is seen to include a stiffening wire 44. In practice, a workable PTCA catheter system may result when a reinforcing strand is incorporated in only one of the two concentric tubes. Typically, the diameter of the reinforcing strand may be 0.001 inch to 0.002 inch while the wall thickness of the outer tubular member may be in the range of from 0.001 to 0.006 inch.

In fabricating the tubes 12 and 20, a solid cylindrical mandrel approximately five feet long may first be coated with multiple thin layers of plastic. While various plastics including polyesters, polyamides and polyimides may be employed, it has been found that polyimide is preferred because of its characteristics of tensile strength and flexibility.

Once the mandrel is so coated, the reinforcing wire(s) 40 or 44 may be positioned on the coating covering the mandrel and then that assembly is repeatedly dipped, sprayed or otherwise coated with additional layers of the same plastic whereby the wire reinforcing strand becomes totally embedded within the tube's wall.

FIG. 2 illustrates how a plurality of strands 40a and 40b can be embedded in the wall of the outer tubular member 12 and, likewise, how plural reinforcing strands 44a and 44b can be embedded in the wall of the inner tubular member 20. In FIG. 2, the strands are shown as being encased in ribs projecting from the exterior walls of the tubes. In the view of FIG. 3, however, the wire reinforcing members 40 and 44 are wholly contained within the walls of the tubes 12 and 20.

The cross-sectional view of FIG. 4 shows a further alternative arrangement. Here, the inner tubular member 20 is seen to include a single reinforcing strand 44 while the outer tubular member 12 incorporates a plurality of wire strands in the form of a loosely woven braid 46. Of course, both tubular members can incorporate braided strands.

Using the approach of the present invention, it has been found possible to construct a coaxial PTCA catheter whose outer tube 12 may have an O.D. as small as 0.026 inch with a wall thickness of about 0.001 inch leaving a lumen of about 0.024 inch in diameter. A lumen of this size can accommodate an inner tube 20 having a O.D. in the range of from 0.0185 inch to 0.021 inch and a corresponding I.D. of from 0.017 inch to 0.0187 inch. The lumen of the inner tube can then accommodate a guide wire 36 whose O.D. may be typically 0.014 inch.

Those skilled in the art will appreciate that the foregoing dimensions are exemplary only and are included to illustrate the fact that by choosing an appropriate plastic material (polyimide) and by incorporating a fine wire strand in the wall of the tube(s) comprising the catheter, a coaxial catheter can be constructed which will have a very low overall outer dimension yet will possess the necessary longitudinal rigidity to as to avoid the tube collapsing in the longitudinal direction and becoming accordion pleated when pushed or advanced through a guide catheter or otherwise through the vascular system. Thus, the wall thickness of each of the concentric tubes may be in the range of from 0.001 to 0.006 inch. The O.D. of the outer tube 12 may then be in the range of from 0.026 to 0.058 inch and that of the inner tube 20 may in the range of from 0.0177 to 0.037 inch.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An intravascular balloon catheter comprising:

(a) a first elongated, flexible tubular member consisting substantially of a first plastic material having a proximal end, a distal end and describing a lumen and a longitudinal axis extending from the proximal end to the distal end, the first tubular member having reinforcing means comprising at least one strand of wire extending parallel to the longitudinal axis of the first tubular member embedded in a wall thereof along substantially the entire length of the first tubular member, said wall having a thickness in the range of about 0.001–0.006 inch, said at least one strand of wire being elastic to allow bending of the first tubular member while being substantially rigid in the longitudinal direction;

(b) a second elongated, flexible tubular member consisting substantially of a second plastic material having a proximal end, a distal end and describing a lumen and a longitudinal axis extending from the proximal end to the distal end, the second tubular member being disposed in the lumen of the first tubular member such that a distal end portion of the second tubular member extends out beyond the distal end of the first tubular and such that an annular space is formed within the lumen of said first flexible tubular member and external to and containing said second flexible tubular member;

(c) an inflatable expander member having a proximal end and a distal end, the proximal end being circumferentially bonded to the first tubular member near the distal end thereof and the distal end of the expander member being circumferentially bonded to the distal end portion of the second tubular member; and (d) a hub member affixed to the proximal ends of the first and second tubular members and including an inflation port in fluid communication with said annular space in the lumen of the first tubular member external to the second tubular member.

2. The catheter of claim 1 further including reinforcing means in the wall of the second tubular member and extending substantially the entire length of the second tubular member.

3. The catheter of claim 2 wherein the reinforcing means in at least one of said first and second tubular members includes a plurality of radially spaced wire strands extending parallel to said longitudinal axis of said first and second tubular members.

4. The catheter of claim 1 wherein the first and second plastic materials are selected from the group of polymers consisting of polyamides, polyimides and polyesters.

5. The catheter of claim 1 wherein said first plastic material is a polyimide.

6. The catheter of claim 1 wherein both of said first and said second plastic materials are polyimines.

7. The catheter of claim 2 wherein the reinforcing means in the second tubular member comprises at least one strand of wire extending parallel to the longitudinal axis of the second tubular member.

8. The catheter of claim 1 wherein the outside diameter of the first tubular member is in the range of from 0.026 to 0.058 inch and the outside diameter of the second tubular member is in the range of from 0.0177 to 0.037 inch.

9. An intravascular dilation catheter comprising:
(a) an outer, flexible, elongate tubular member having a proximal end, a distal end and defining a longitudinal axis therealong and describing a lumen therealong and having stiffening means comprising at least one first wire extending generally parallel to the longitudinal axis of the outer tubular member embedded in the wall of the outer tubular member and extending from the proximal end to the distal end, wherein said wall has a thickness in the range of about 0.001–0.006 inch, and said at least one first wire has a diameter at most equal to said thickness and is substantially rigid in the longitudinal direction while being elastic to allow bending of the outer tubular member;

(b) an inner, flexible, elongate tubular member having a proximal end, a distal end and defining a longitudinal axis therealong and describing a lumen therealong and having stiffening means comprising at least one second wire extending generally parallel to the longitudinal axis of the inner tubular member embedded in the wall of the inner tubular member and extending from the proximal end to the distal end, the inner tubular member being coaxially disposed in the lumen of the outer tubular member with a predetermined clearance between the outer and inner tubular members with a distal end portion of the inner tubular member extending beyond the distal end of the outer tubular member, wherein said at least one second wire has a diameter at most equal to a wall thickness of the inner tubular member and is substantially rigid in the longitudinal direction while being elastic to allow bending of the inner tubular member; and (c) a tubular, inflatable expander member having a proximal end and a distal end, the proximal end of the expander member being circumferentially bonded to the wall of the outer tubular member and the distal end of the expander member being circumferentially bonded to the wall of the inner tubular member at a location on the distal end portion of the inner tubular member.

10. The catheter of claim 9 wherein the outer and inner tubular members consist substantially of polymers selected from the group including polyamides, polyimides and polyesters plastic.

11. The catheter of claim 9 wherein said stiffening means in each of said inner and outer tubular members comprises two or more fine wires extending longitudinally from said distal ends to said proximal ends and parallel to the longitudinal axes of said outer and inner tubular members.

12. The catheter of claim 9 wherein the O.D. of the outer tubular member is in the range of from 0.028 to 0.058 inch and the wall thickness of the outer tubular member is in the range of from about 0.001 to 0.005 inch.

13. The catheter of claim 12 wherein the O.D. of the inner tubular member is in the range of from 0.0177 to 0.037 inch and the wall thickness of the inner tubular member is in the range of from about 0.001 to 0.005 inch.

14. An intravascular balloon catheter comprising:
(a) a first elongated, flexible plastic tubular member having a proximal end and a distal end, and describing a lumen extending from the proximal end to the distal end, and having a wall with a thickness in the range of about 0.001 to 0.006 inch;

(b) a second elongated, flexible plastic tubular member having a proximal end, a distal end and a longitudinal axis, and describing a lumen extending from the proximal end to the distal end, the second tubular member including reinforcing means embedded in the wall thereof along substantially the entire length of the second tubular member, said reinforcing means having a radial dimension in the range of about 0.001 to 0.002 inch and being elastic to allow bending of the second tubular member while being substantially rigid in the longitudinal direction, the second tubular member further being disposed in the lumen of the first tubular member to form an annular space between said first and second tubular members and disposed such that a distal end portion of the second tubular member extends a distance beyond the distal end of the first tubular member;

(c) an inflatable expander member having a proximal end and a distal end, the proximal end being circumferentially bonded to the exterior wall of the first tubular member near the distal end thereof and the distal end of the expander member being circumferentially bonded to the distal end portion of the second tubular member; and (d) a hub member affixed to the proximal ends of said first and second tubular members with said hub member including an inflation port in fluid communication with said annular space in the lumen of said first tubular member surrounding the second tubular member.

15. An intravascular dilation catheter comprising:

(a) an outer, flexible, elongate tubular member having a proximal end, a distal end and defining a longitudinal axis therealong and describing a lumen therealong and having stiffening means comprising a longitudinally oriented steel wire embedded in the wall of the outer tubular member and extending from the proximal end to the distal end, wherein the outer tubular member has an outer diameter in the range of 0.028 to 0.058 inch, and a wall thickness in the range of about 0.001 to 0.006 inch, said stainless steel wire having a diameter in the range of 0.001 to 0.002 inch;

(b) an inner, flexible, elongate tubular member having a proximal end, a distal end and defining a longitudinal axis therealong and describing a lumen therealong and having stiffening means embedded in the wall of the inner tubular member and extending from the proximal end to the distal end, the inner tubular member being coaxially disposed in the lumen of the outer tubular member with a predetermined clearance between the outer and inner tubular members with a distal end portion of the inner tubular member extending beyond the distal end of the outer tubular member; and (c) a tubular, inflatable expander member having a proximal end and a distal end, the proximal end of the expander member being circumferentially bonded to the wall of the outer tubular member and the distal end of the expander member being circumferentially bonded to the wall of the inner tubular member at a location on the distal end portion of the inner tubular member.

* * * * *